(12) United States Patent
Kuo

(10) Patent No.: US 10,004,649 B2
(45) Date of Patent: Jun. 26, 2018

(54) ABSORBENT PANTS

(71) Applicant: Chien-Chung Chen, New Taipei (TW)

(72) Inventor: Shih Huey Kuo, New Taipei (TW)

(73) Assignee: Chien-Chung Chen, New Taipei (TW)

( * ) Notice: Subject to any disclaimer, the term of this patent is extended or adjusted under 35 U.S.C. 154(b) by 407 days.

(21) Appl. No.: 14/792,618

(22) Filed: Jul. 7, 2015

(65) Prior Publication Data

US 2017/0007474 A1  Jan. 12, 2017

(51) Int. Cl.
| | |
|---|---|
| *A61F 13/66* | (2006.01) |
| *A61F 13/76* | (2006.01) |
| *A41D 13/12* | (2006.01) |
| *A61F 13/49* | (2006.01) |
| *A61F 13/64* | (2006.01) |
| *A41D 15/00* | (2006.01) |
| *A61F 13/56* | (2006.01) |

(52) U.S. Cl.
CPC .......... *A61F 13/76* (2013.01); *A41D 13/1254* (2013.01); *A41D 15/002* (2013.01); *A61F 13/4906* (2013.01); *A61F 13/49006* (2013.01); *A61F 13/5655* (2013.01); *A61F 13/64* (2013.01); *A61F 13/66* (2013.01); *A41D 2400/44* (2013.01); *A61F 2013/5627* (2013.01)

(58) Field of Classification Search
CPC ............ A61F 13/49006; A61F 13/5655; A61F 13/64; A61F 13/66; A61F 13/70; A61F 13/76; A61F 13/78; A61F 2013/5627; A61F 2013/5672; A41D 15/002; A41D 13/1254
See application file for complete search history.

(56) References Cited

U.S. PATENT DOCUMENTS

| | | | | |
|---|---|---|---|---|
| 5,241,708 | A  * | 9/1993 | Rodarmel | A61F 5/3769 |
| | | | | 2/227 |
| 5,706,523 | A  * | 1/1998 | Witzel | A41D 13/0506 |
| | | | | 2/227 |
| 5,926,851 | A  * | 7/1999 | Kovalik | A41D 1/06 |
| | | | | 2/114 |
| 8,679,085 | B2 * | 3/2014 | Ronstrom | A61F 13/505 |
| | | | | 604/385.14 |
| 2001/0004771 | A1 * | 6/2001 | Chou | A41D 1/007 |
| | | | | 2/227 |

* cited by examiner

*Primary Examiner* — Lynne Anderson
(74) *Attorney, Agent, or Firm* — Leong C. Lei

(57) ABSTRACT

The pants has two zippers symmetrically arranged from a waistband's front center extend slantwise downward to a lateral side of the pants. A detachable wrapping member is integrated with the pants. The wrapping member has a belt whose two ends thread through corresponding loops at bottom corners of the wrapping member, and a bottom portion of the wrapping member is flipped upward to reliably cover a crotch area of a user, preventing excrement or urine from overflowing. A clamping member uses Velcro fastening elements or snap buttons to lock a planar object of an absorbent member, and the clamping member can provide secured positioning, increased friction, and load distribution so that the absorbent member can be reliably worn. The clamping member contains a clamping element that is concealed when not in use. The clamping element then can be flipped to further secure its locking the absorbent member.

3 Claims, 11 Drawing Sheets

ABSORBENT PANTS

BACKGROUND OF THE INVENTION (a) Technical Field of the Invention

The present invention is generally related to adult absorbent devices, and more particular to an absorbent pants with detachable wrapping member and absorbent member.

(b) Description of the Prior Art

Conventional adult diapers contains a permeating inner layer, a waterproof outer layer, and an absorbent layer sandwiched in-between. The conventional adult diapers usually have oversized waist and upper abdomen portions which is not economical and environmentally friendly. In addition, a large number of users of adult diapers are people who are bedridden or in wheelchairs. On the average, they need to change their diapers seven times a day, placing significant load to health care personnel. In general, conventional adult diapers have the following disadvantages: (1) they are not environmentally friendly; (2) they are costly; (3) they provide poor ventilation; (4) they provide insufficient protection; (5) their appearance is inferior; and (6) they are difficult to change.

SUMMARY OF THE INVENTION

A novel absorbent pants is provided to obviate the shortcomings of the prior arts. The absorbent pants provides the following features.

The pants has two zippers symmetrically arranged from a waistband's front center extend slantwise downward to a lateral side of the pants and then straight down for an appropriate distance, respectively, thereby forming a openable front piece that can be separated from a back piece of the pants. Therefore, care to the crotch, buttock, and abdomen can be conducted without taking down the pants. A detachable wrapping member can be worn alone or integrated with the pants.

The wrapping member has a belt whose two ends thread through corresponding loops at bottom corners of the wrapping member, and a bottom portion of the wrapping member is flipped upward to reliably cover a crotch area of a user, preventing excrement or urine from overflowing. An absorbent member of the present invention as such can be reduced in size. The wrapping member can be replaced independently and can integrate with conventional absorbent devise or pants.

The clamping member uses Velcro fastening elements or snap buttons to lock a planar object of the absorbent member, and the clamping member can provide secured positioning, increased friction, and load distribution so that the absorbent member can be reliably worn. The clamping member contains a clamping element that is concealed when not in use. To use the clamping element, it is then exposed so that its Velcro fastening elements or snap buttons can engages the planar object of the absorbent member. The clamping element then can be flipped to further secure its locking the absorbent member. For a clamping element using snap buttons, it can be installed upside down and flipped to lock a conventional absorbent device.

The absorbent member has the planar object extended from between an inner fabric layer and an outer waterproof layer for clamping by the clamping element. After clamping, the clamping element can be flipped to further secure the clamping. Then the absorbent member is folded by the wrapping member. The absorbent member as such can be reliably worn without relying on oversized waist and upper abdomen portions, achieving material reduction and environment friendliness.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
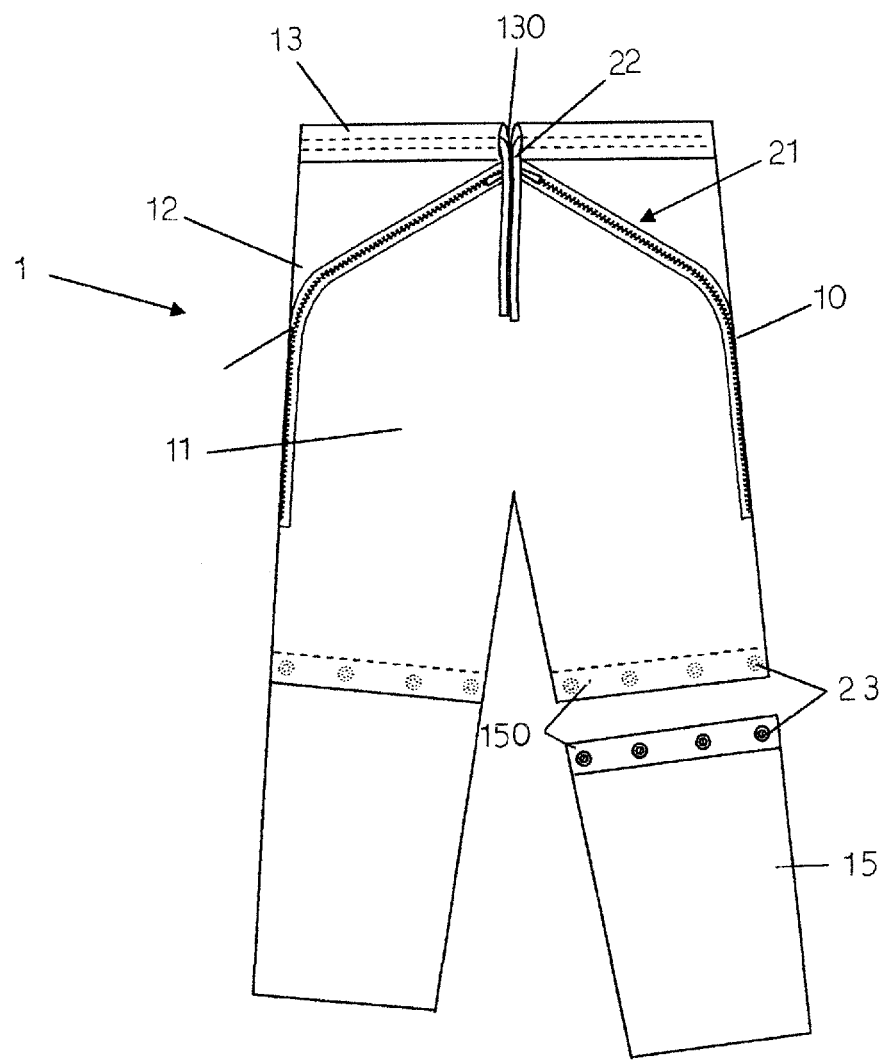
FIG. 1 is a front-view diagram showing an absorbent pants according to an embodiment of the present invention.

As shown in FIG. 1, an absorbent pants 1 according to an embodiment of the present invention contains a waistband 13 with a rope 22 threaded through. The two ends of the rope 22 are exposed through openings 130 at a front center location of the waistband 13. Two zippers 21 are symmetrically arranged that extend from beneath the openings 130 slantwise downward to a lateral side 10 of the pants 1 and then straight down for an appropriate distance, respectively, thereby forming a openable front piece 11 that can be separated from a back piece 12 of the pants 1. The pants 1 has a detachable means 150 around a middle section of each leg. The detachable means 150 involves a number of snap buttons 23 so that a bottom section 15 of each leg can be detached and the pants 1 as such turns into a briefs.

Figure 2:
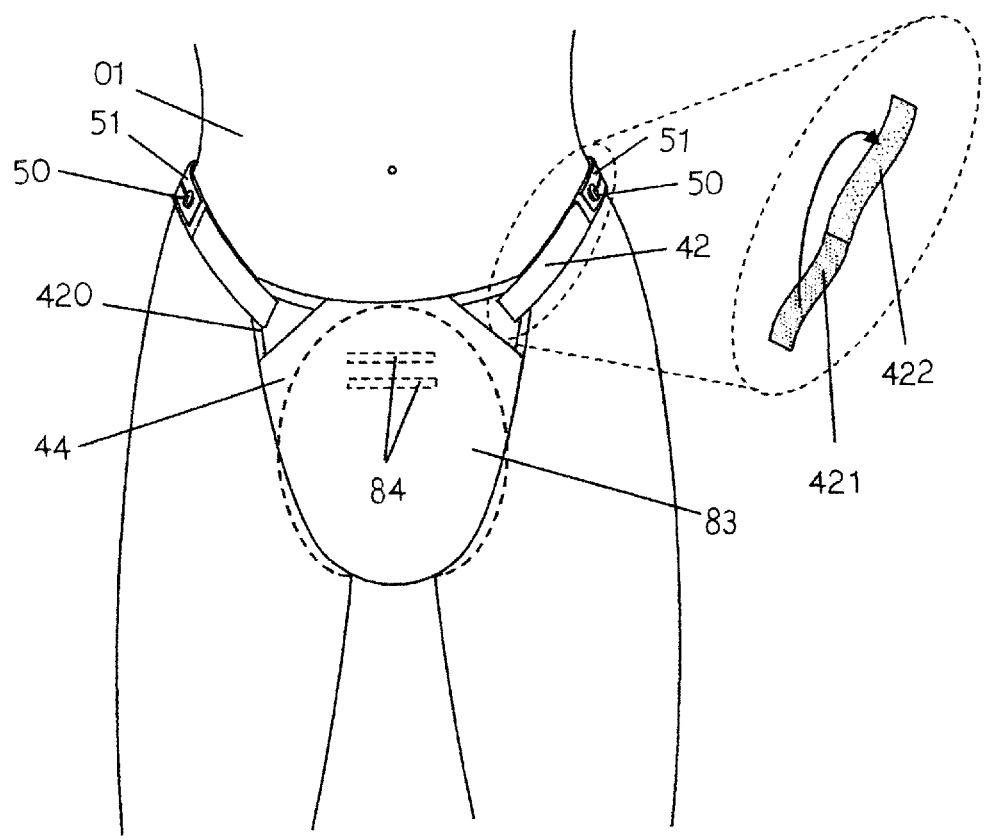
FIG. 2 is a front-view diagram showing a wrapping member and an absorbent member according to an embodiment of the present invention jointly worn by a user.
Figure 3:
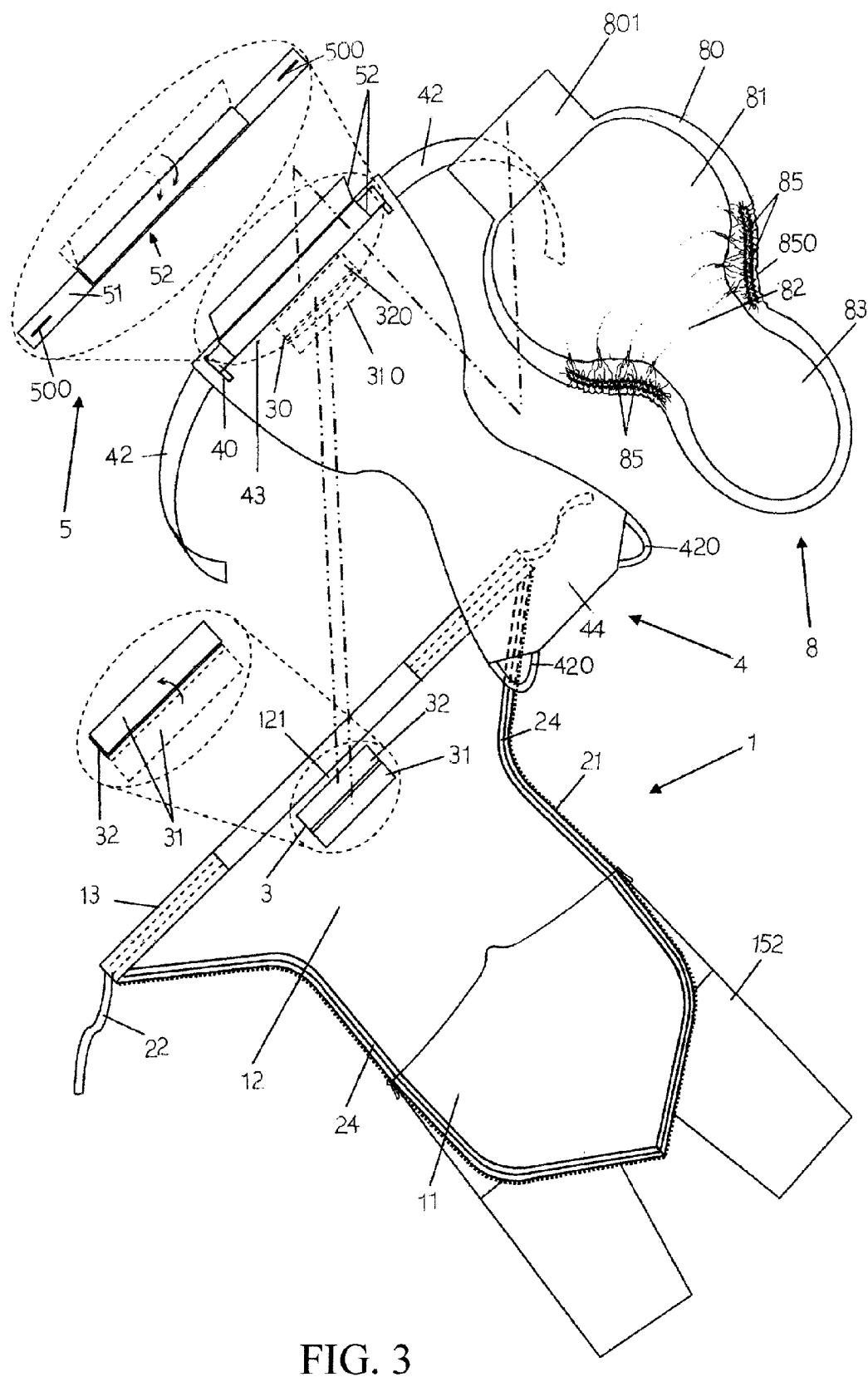
FIG. 3 is a break-down diagram showing the various components of the absorbent pants of FIG. 1.
Figure 10A:
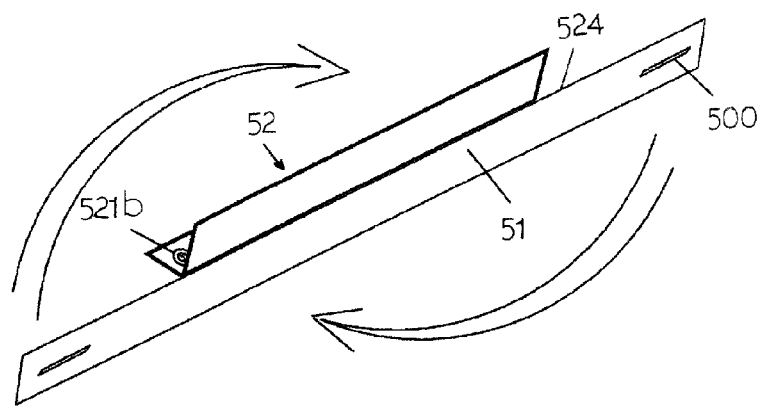
FIGS. 10A and 10B show the installation of a clamping element with snap buttons according to an embodiment of the present invention in two manners.

As shown in FIGS. 2 and 3, each zipper 21 is covered by a flap 24. A fastener 3 is configured on the back piece 12 at an upper center location 121. The fastener 3, such as a Velcro fastener, contains a first fastening element 31 and a matching second fastening element 32 where the first fastening element 31 can be flipped to cover the second fastening element 32 so that the rough surfaces of the first and second fastening elements 31 and 32 do not contact a user's skin. When the second fastening element 32 is not covered, a corresponding fastener 30 on an outside surface of a wrapping member 4 with matching fastening elements 310 and 320 can be joined to the first and second fastening elements 31 and 32 of the fastener 3. The wrapping member 4 has a top portion 43, a bottom portion 44, and a belt 42 running along a top edge of the top portion 42 whose two ends thread through corresponding loops 420 located at bottom corners of the bottom portion 44. Each end of the belt 42 has a button 50 and fastening elements 422 and 421 sequentially arranged on an outer side of the belt 42. Therefore, after threading through a loop 420, an end of the belt 42 is turned around so that the fastening element 421 is locked to the fastening element 422 and the bottom portion 44 of the wrapping member 4 is flipped to cover a crotch area of the user. A clamping member 5 is configured along the belt 42. The clamping member 5 contains a strip 51 with a slit 500 at each end and a clamping element 52 along a top edge 524 of the strip 51 (as shown in FIG. 10A). A clamping piece 801 of an absorbent member 8 is clamped by the clamping element 52. The absorbent member 8 is then attached to the bottom portion 44 by at least an adhesive strip 84 on an outer side of the absorbent member 8. The wrapping member 4 can be made of a highly flexible fabric with moisture absorption and quick drying capability.

Figure 4:
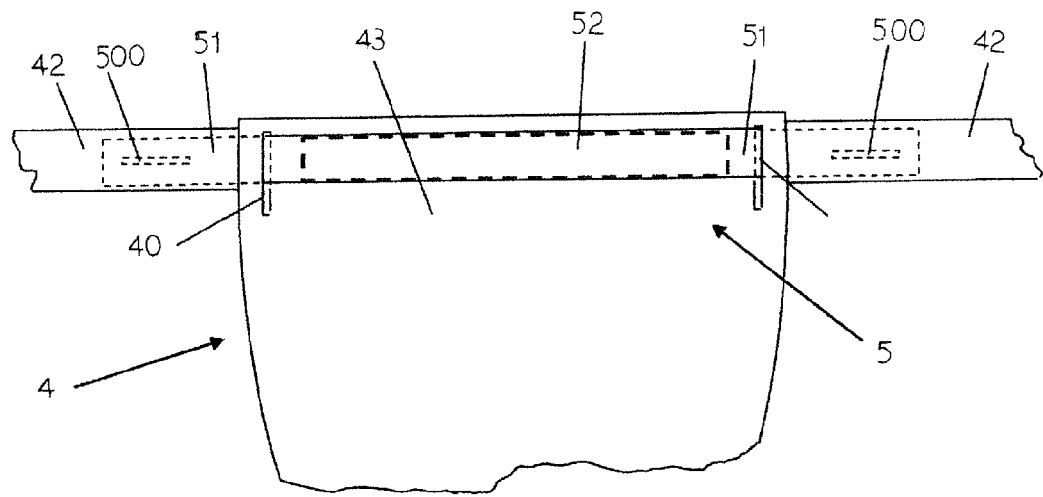
FIG. 4 is a schematic diagram showing a clamping element according to an embodiment of the present invention.
Figure 5:
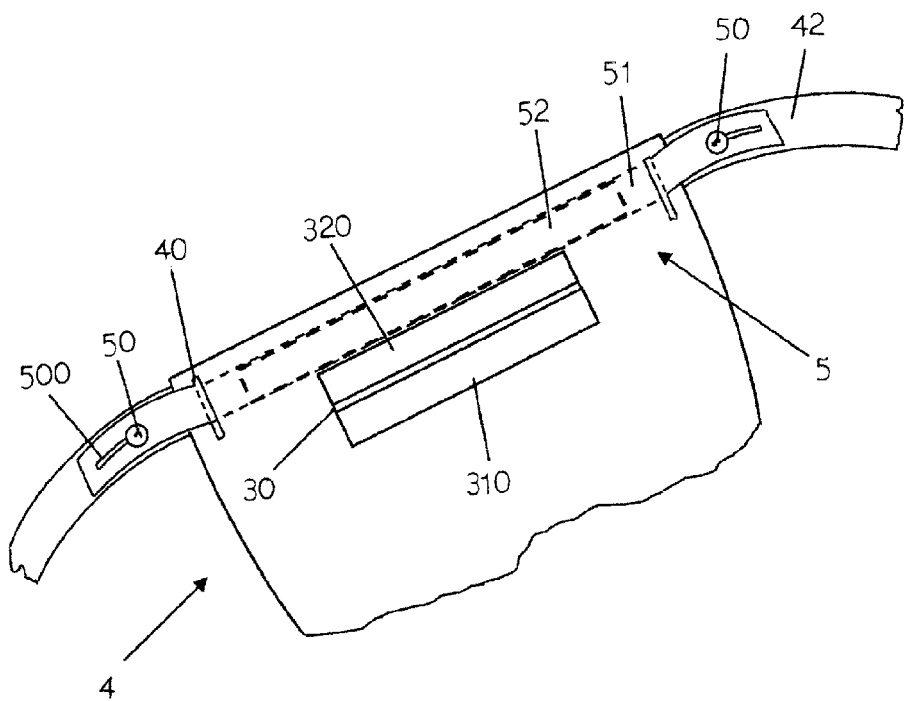
FIG. 5 is a schematic diagram showing the clamping element of FIG. 4 viewed from an opposite side.

As shown in FIGS. 4 and 5, each end of the belt 42 runs through two slits 40 at the two ends of the top edge of the top portion 43, respectively. The clamping member 5 has its slips 500 locked to the buttons 50. The clamping element 52 can be hidden between the strip 51 and the wrapping member 4 when not in use. The fastener 30 is located on an outside surface of the wrapping member 4 below the belt 42 and the clamping member 5.

Figure 6:
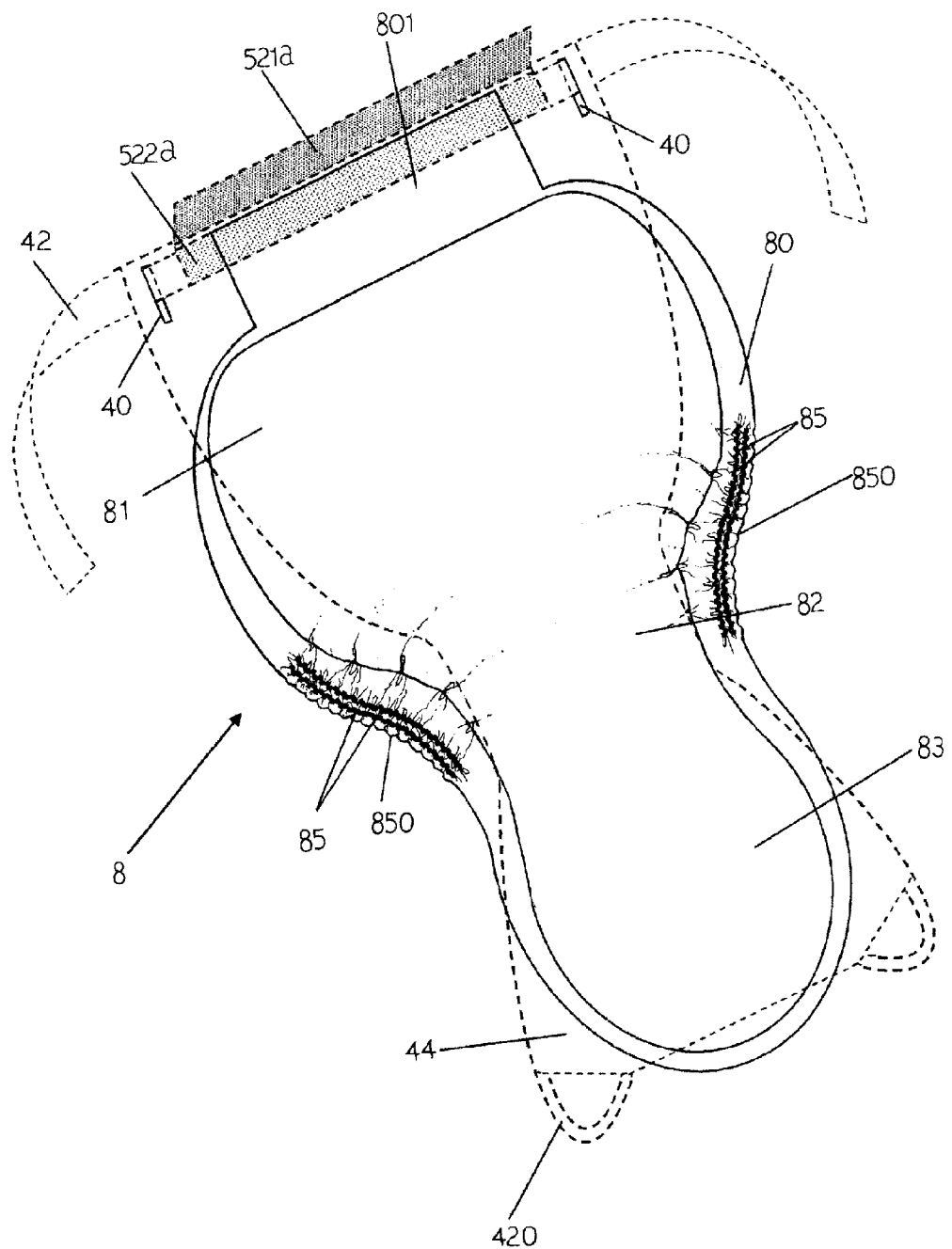
FIG. 6 is a schematic diagram showing an absorbent member joined to a wrapping member according to an embodiment of the present invention using Velcro fastening elements.
Figure 7:
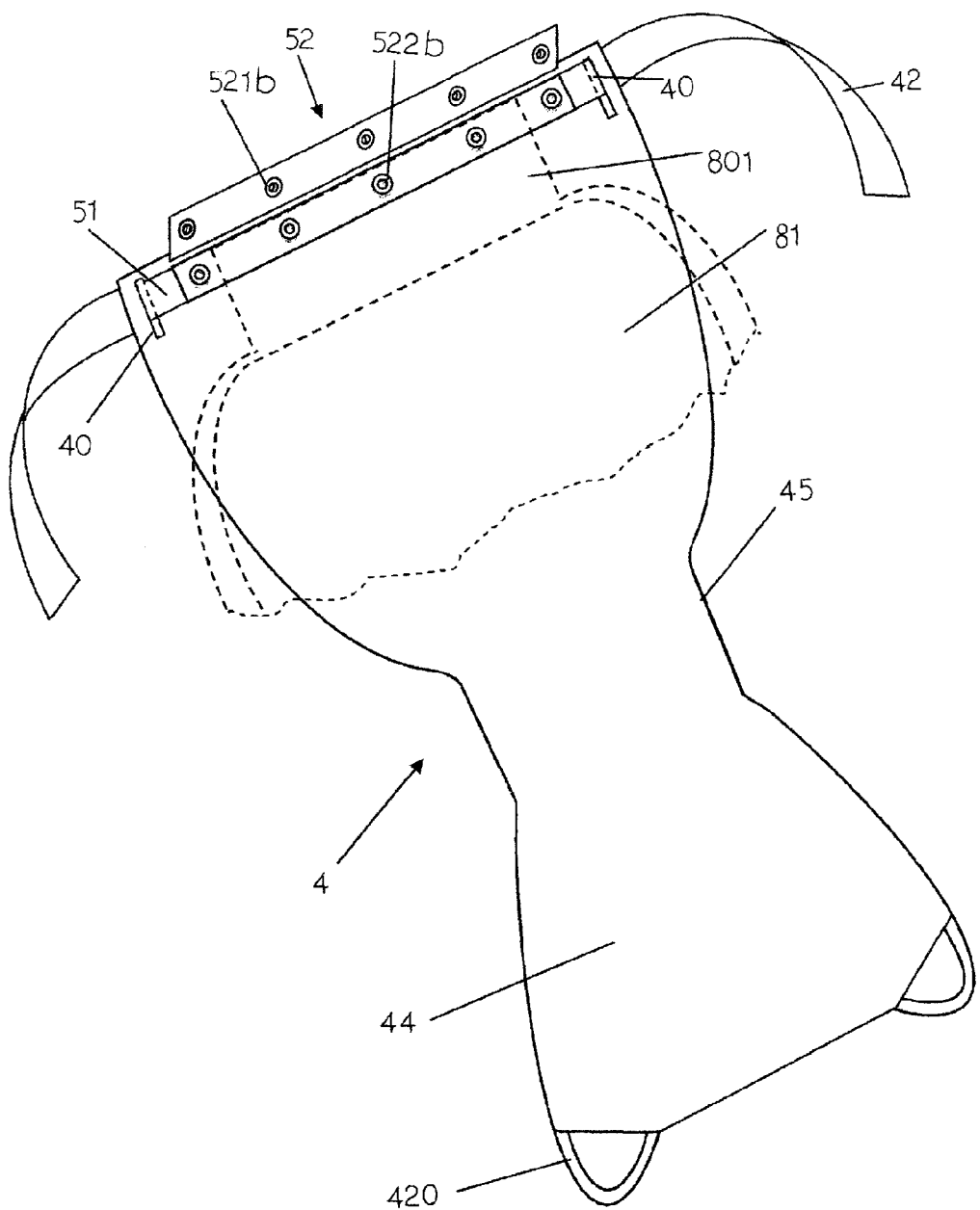
FIG. 7 is a schematic diagram showing an absorbent member joined to a wrapping member according to an embodiment of the present invention using snap buttons.

As shown in FIGS. 6 and 7, the absorbent member 8 contains a non-woven fabric as an inner layer, a waterproof outer layer, and an absorbent layer sandwiched therebetween, and has a buttock portion 81, a crotch portion 82, and a lower abdomen portion 83. The clamp piece 801 is a planar object extended from a top edge of the buttock portion 81. A flange 80 is extended along each lateral side of the absorbent member 8. Each flange 80 has an elastic band 85 on an inner side from a lower part of the buttock portion 81 to an upper part of the crotch portion 82, thereby forming a tightening rim 850. To install the absorbent member 8 on the wrapping member 4, a top portion of the clamping piece 801 is clamped between the clamping element 52. As shown in FIG. 6, the clamping element 52 contains two matching Velcro fastening elements 521a and 522a where the clamping piece 801 is sandwiched in-between. Alternatively, as shown in FIG. 7, the clamping element 52 contains two strips 521b and 522b with matching snap buttons.

Figure 8A:
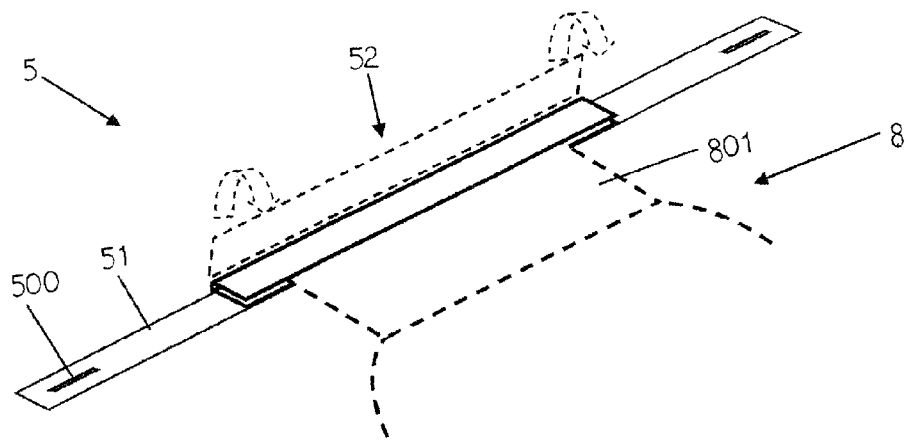
FIGS. 8A~8C show a scenario that a clamping piece of an absorbent member is clamped and secured by a clamping element of a wrapping member according to an embodiment of the present invention.
Figure 8B:
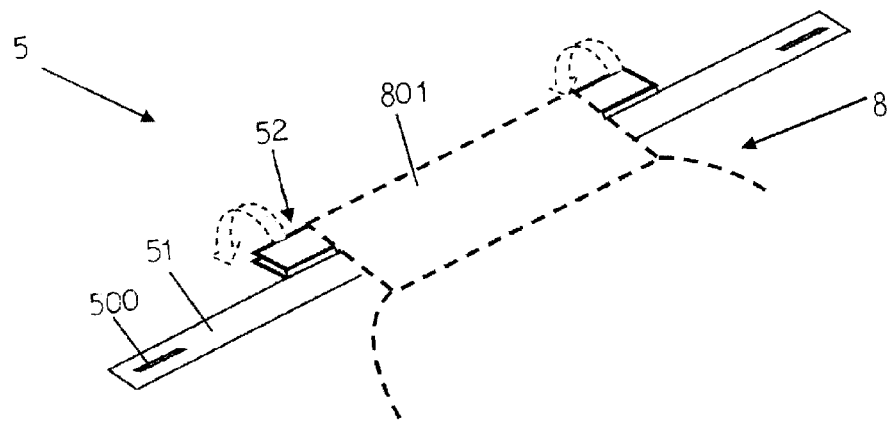
Figure 8C:
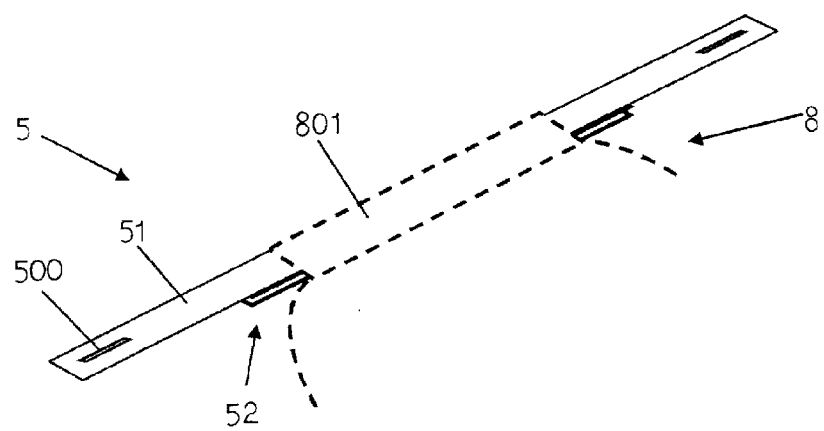

As shown in FIGS. 8A-8C, the clamping piece 801 of the absorbent member 8 is secured as follows. The clamping element 52 is flipped to a front side of the strip 51. After the clamping piece 801 is clamped by the clamping element 52, the clamping element 52 is flipped from the front side of the strip 51 to an opposite back side of the strip 51.

Figure 9:
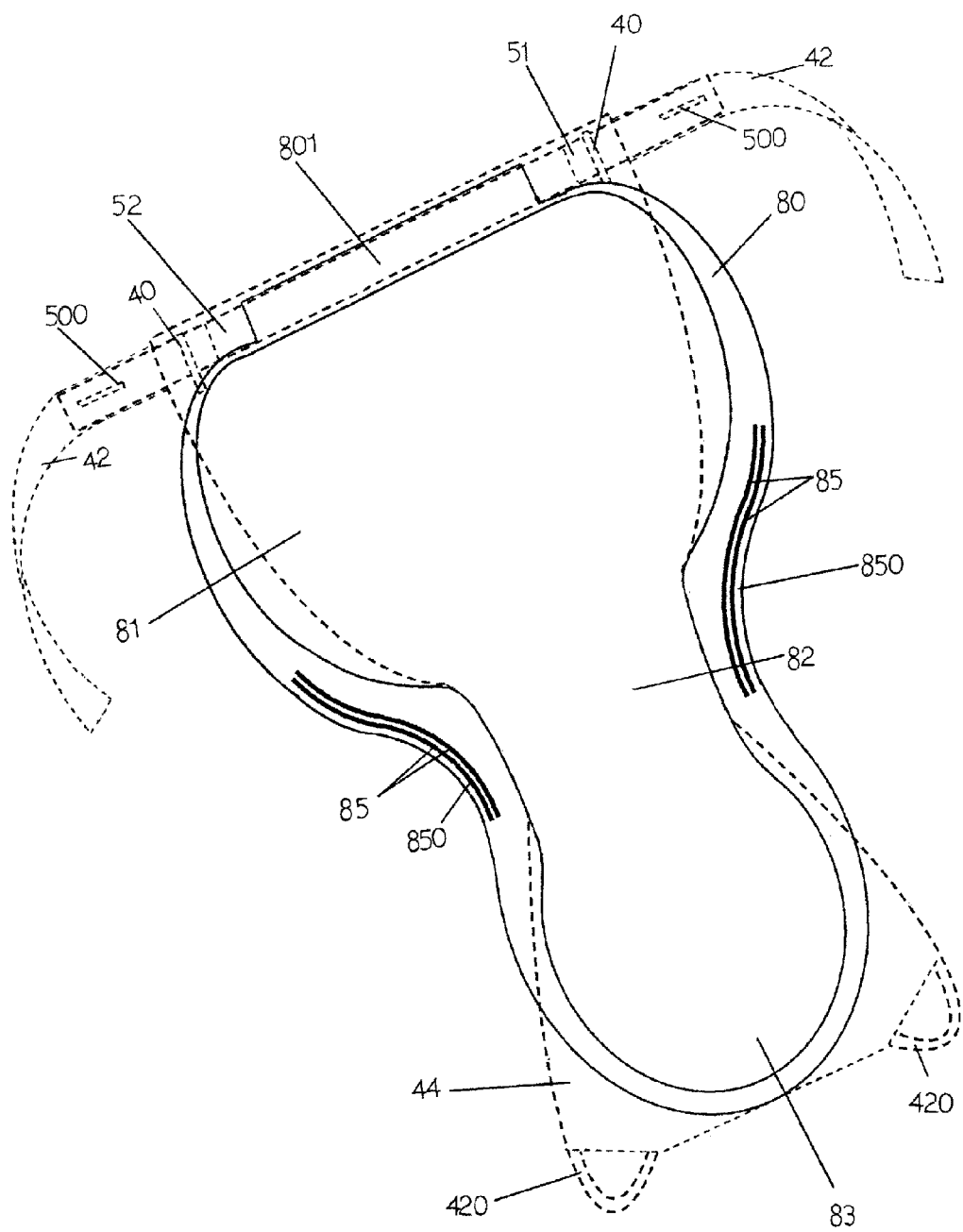
FIG. 9 is a schematic diagram showing an absorbent member and a wrapping member according to an embodiment of the present invention after their assembly.

As shown in FIG. 9, after the clamping piece 801 of the absorbent member 8 is secured as described above, the absorbent member 8 is then attached to the bottom portion 44 of the wrapping member 4 by at least an adhesive strip 84 on the outer side of the absorbent member 8. At the moment, the tightening rims 850 may be stretched. But once a user puts on the pants 1, the tightening rims 850 may quickly shrink to closely enclose the crotch of the user.

Figure 10B:
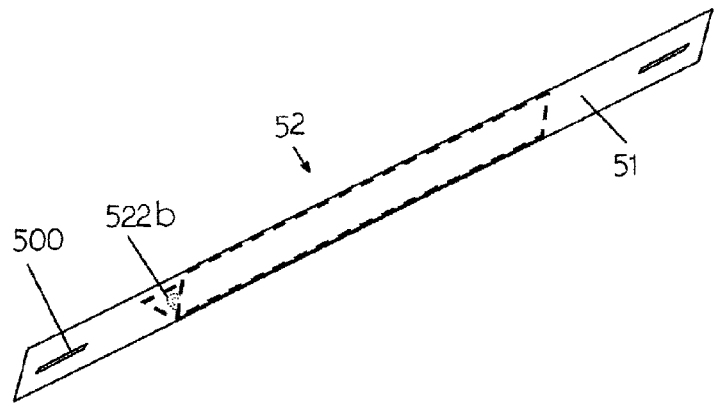

As shown in FIG. 10A, the clamping member 5 is installed with the clamping element 52 located along the top edge of the strip 51. Alternatively, as shown in FIG. 10B, the clamping member 5 can be installed upside down.

Figure 11:
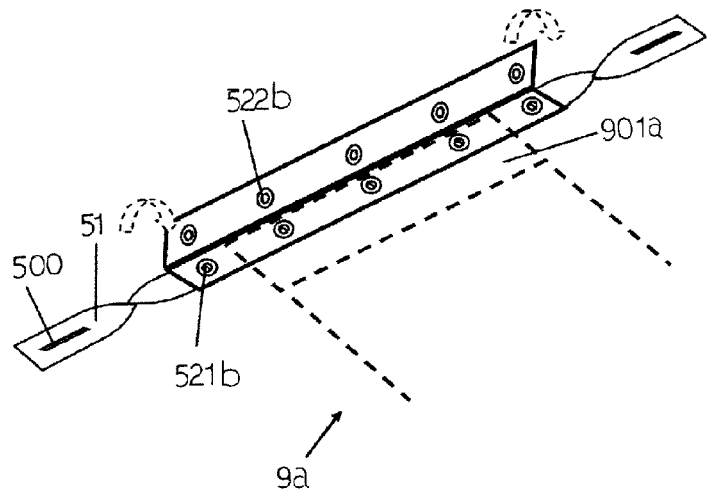
FIGS. 11 and 12 show a scenario that a conventional absorbent device is joined to a wrapping member according to an embodiment of the present invention using snap buttons.
Figure 12:
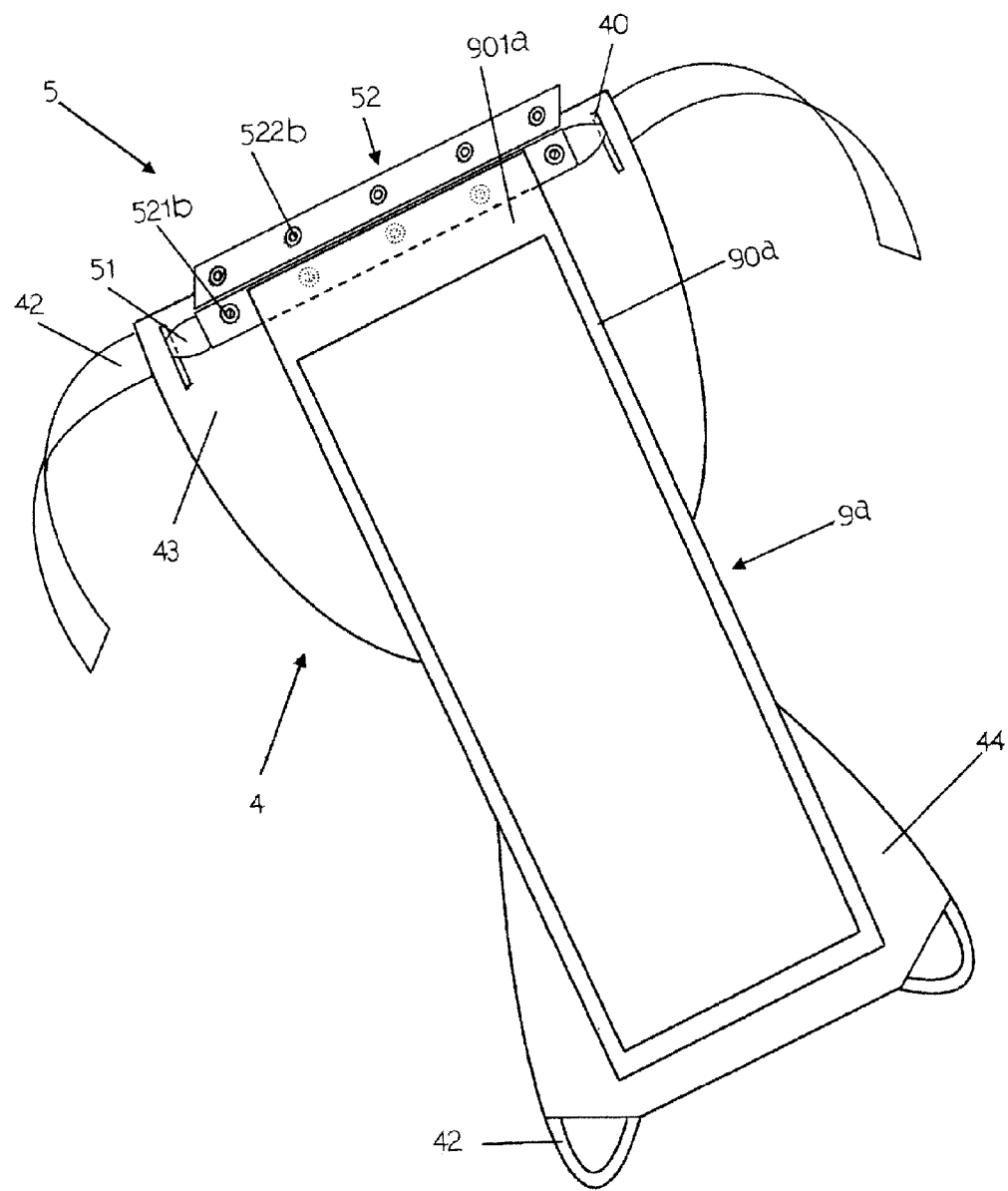

If the clamping member 5 is installed as shown in FIG. 110B, it can still provide clamping as shown in FIG. 11 by turning the strip 51 around. Please note that the slits 500 has an appropriate length so as to provide the leeway required by the flipping of the strip 51. As shown in FIGS. 11 and 12, instead of the absorbent member 8 of the present invention, the wrapping member 4 can be used with conventional absorbent device 9a where a side portion 901a is clamped by the flip-around clamping element 52. After clamping, the clamping element 52 can be flipped back to its original location.

Figure 13:
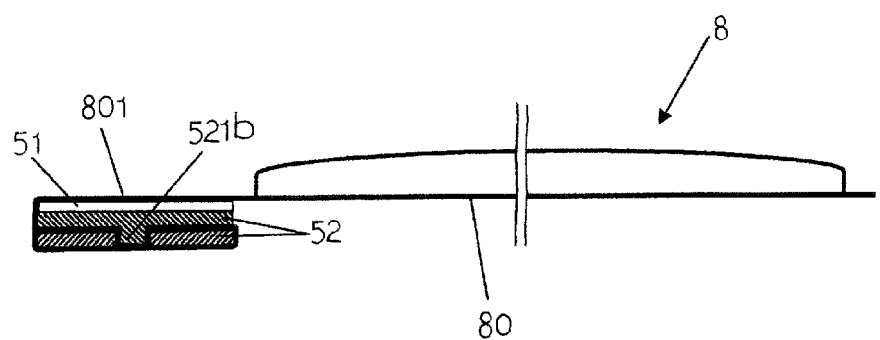
FIG. 13 is a sectional diagram showing an absorbent member clamped by a clamping element according to an embodiment of the present invention.
Figure 14:
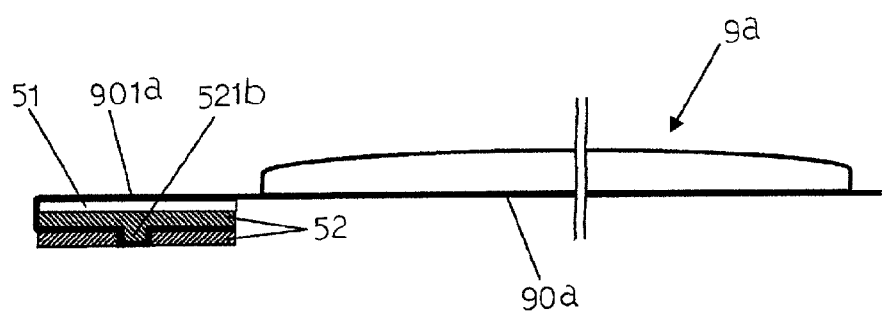
FIG. 14 is a sectional diagram showing a conventional absorbent device clamped by a clamping element according to an embodiment of the present invention.
Figure 15:
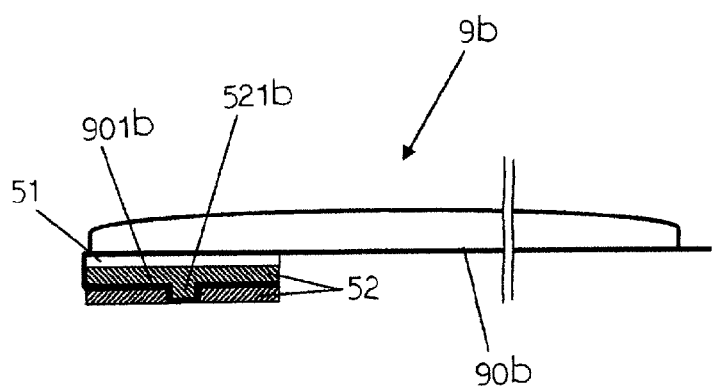
FIG. 15 is a sectional diagram showing a conventional absorbent device clamped by a clamping element according to an embodiment of the present invention in a different manner.

The heights of the strip 51 and the clamping element 52 are preferably 2.5 cm so as to appropriately clamp the clamping piece 801 and to flip around as shown in FIG. 13 where the height of the clamping piece 801 is about 8.5~9 cm. Similarly, the clamping element 52 can properly clamp the side portion 901a of a conventional absorbent device 9a and flip around, as shown in FIG. 14, where the height of the side portion 901a is about 5.5~6 cm. Alternatively, as described above, the clamping element 52 can be installed in an upside-down manner. In this way, the clamping element 52 can properly clamp a side portion 901b of a conventional absorbent device 9b and flip back, as shown in FIG. 15, where the height of the side portion 901b is about 2.5~3 cm.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:
1. An absorbent pants comprising:
a waistband;

two zippers symmetrically extend from waistband's front center slantwise downward to a lateral side of the pants end and then straight down for an appropriate distance, respectively, thereby forming a openable front piece that can be separated from a back piece of the pants;

a fastener configured on the back piece comprising a first fastening element and a matching second fastening element where the first fastening element is capable of being flipped to cover the second fastening element;

two legs, each having a detachable means around a middle section so that a bottom section of each leg is detachable;

a wrapping member comprising a top portion, a bottom portion, matching fastening elements detachably joined to the first and second fastening elements of the fastener, a belt running along a top edge through two slits at two ends of the top edge of the top portion whose two ends thread through corresponding loops located at bottom corners of the bottom portion, where each end of the belt has a button and fastening elements sequentially arranged on an outer side of the belt;

a clamping member configured along the belt where the clamping member comprises a strip with a slit at each end and a clamping element along a top edge of the strip, where the clamping member has its slips locked to the buttons; and an absorbent member comprising a non-woven fabric as an inner layer, a waterproof outer layer, an absorbent layer sandwiched therebetween, and a clamp piece, where the absorbent member has a buttock portion, a crotch portion, and a lower abdomen, and the clamp piece is a planar object extended from a top edge of the buttock portion, and is clamped by the clamping element.

2. The absorbent pants according to claim 1, wherein the clamping element comprises two matching hook and loop fastening elements or two strips with matching snap buttons.

3. The absorbent pants according to claim 1, wherein a flange is extended along each lateral side of the absorbent member; each flange has an elastic band on an inner side from a lower part of the buttock portion to an upper part of the crotch portion, thereby forming a tightening rim.

* * * * *